(12) United States Patent
Bomzon et al.

(10) Patent No.: US 11,369,790 B2
(45) Date of Patent: Jun. 28, 2022

(54) DELIVERING ALTERNATING ELECTRIC FIELDS (E.G., TTFIELDS) TO A SUBJECT'S SPINAL ANATOMY

(71) Applicant: Novocure GmbH, Root (CH)

(72) Inventors: Zeev Bomzon, Kiryat Tivon (IL); Ariel Naveh, Haifa (IL); Ofir Yesharim, Nes Tziona (IL)

(73) Assignee: Novocure GmbH, Root (CH)

( * ) Notice: Subject to any disclaimer, the term of this patent is extended or adjusted under 35 U.S.C. 154(b) by 133 days.

(21) Appl. No.: 16/664,308

(22) Filed: Oct. 25, 2019

(65) Prior Publication Data

US 2020/0129761 A1 Apr. 30, 2020

Related U.S. Application Data

(60) Provisional application No. 62/781,358, filed on Dec. 18, 2018, provisional application No. 62/750,315, filed on Oct. 25, 2018.

(51) Int. Cl.
*A61N 1/36* (2006.01)
*A61N 1/04* (2006.01)

(52) U.S. Cl.
CPC ....... *A61N 1/36002* (2017.08); *A61N 1/0408* (2013.01); *A61N 1/36034* (2017.08)

(58) Field of Classification Search
CPC .. A61N 1/0408; A61N 1/0526; A61N 1/0529; A61N 1/0531; A61N 1/0534; A61N 1/0551; A61N 1/36002; A61N 1/36034
See application file for complete search history.

(56) References Cited

U.S. PATENT DOCUMENTS

| | | | |
|---|---|---|---|
| 6,169,924 B1 * | 1/2001 | Meloy | A61N 1/36017 607/39 |
| 6,868,289 B2 | 3/2005 | Palti | |
| 7,016,725 B2 | 3/2006 | Palti | |
| 7,089,054 B2 | 8/2006 | Palti | |
| 7,136,699 B2 | 11/2006 | Palti | |

(Continued)

OTHER PUBLICATIONS

International Search Report and Written Opinion issued in application No. PCT/IB2019/059189 dated Dec. 19, 2019.

*Primary Examiner* — Carl H Layno
*Assistant Examiner* — Anh-Khoa N Dinh
(74) *Attorney, Agent, or Firm* — Potomac Law Group, PLLC

(57) ABSTRACT

This application discloses an improved approach for delivering alternating electric fields (e.g., TTFields) at a therapeutically effective strength to a target region of the spinal anatomy. In some embodiments, first and second sets of electrode elements are positioned with their centroids adjacent to upper and lower portions of the person's spine, respectively. In other embodiments, a first set of electrode elements is positioned with its centroid on an upper surface of the person's head, and a second set of electrode elements is positioned with its centroid adjacent to the person's spine (e.g., below the L3 vertebrae). Applying an AC voltage between the first and second sets of electrode elements generates a generally vertical field in the target region at levels that are not achievable using other layouts for positioning the electrode elements on the subject's body. These configurations are particularly useful for preventing and/or treating metastases.

8 Claims, 5 Drawing Sheets

(56) References Cited

U.S. PATENT DOCUMENTS

| | | |
|---|---|---|
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 * | 2/2011 | Palti .................. A61N 1/326 607/76 |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 2005/0125045 A1 * | 6/2005 | Brighton ................ A61N 1/326 607/51 |
| 2006/0167499 A1 | 7/2006 | Palti |
| 2007/0225766 A1 | 9/2007 | Palti |
| 2007/0239213 A1 * | 10/2007 | Palti .................. A61K 41/0052 607/3 |
| 2008/0208287 A1 * | 8/2008 | Palermo ............... A61N 1/0526 607/48 |
| 2012/0283726 A1 | 11/2012 | Palti |
| 2016/0022986 A1 * | 1/2016 | Travers .................. A61N 1/40 607/59 |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 * | 1/2018 | Kirson .................. A61N 1/40 |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |

* cited by examiner

DELIVERING ALTERNATING ELECTRIC FIELDS (E.G., TTFIELDS) TO A SUBJECT'S SPINAL ANATOMY

CROSS REFERENCE TO RELATED APPLICATIONS

This application claims the benefit of U.S. Provisional Applications 62/750,315 (filed Oct. 25, 2018) and 62/781,358 (filed Dec. 18, 2018) each of which is incorporated herein by reference in its entirety.

BACKGROUND

TTFields are low intensity (e.g., 1-4 V/cm) alternating electric fields within the intermediate frequency range (e.g., 100-300 kHz), which may be used, for example, to treat tumors as described in U.S. Pat. No. 7,565,205, which is incorporated herein by reference in its entirety. TTFields therapy is an approved mono-treatment for recurrent glioblastoma (GBM), and an approved combination therapy with chemotherapy for newly diagnosed GBM patients. TTFields can also be used to treat tumors in other parts of a person's body (e.g. lungs, ovaries, pancreas). TTFields are induced non-invasively into the target region by transducer arrays (i.e., arrays of capacitively coupled electrode elements) placed directly on the patient's body (e.g., using the Novocure Optune™ system), and applying AC voltages between the transducer arrays.

FIGS. 1 and 2 depict an example of a prior art layout for positioning the transducer arrays on a patient's body for treating a tumor in the patient's thorax and/or abdomen. In this layout, first and second transducer arrays are positioned on the front and back of the patient's thorax and/or abdomen, respectively (as seen in FIG. 1); and third and fourth transducer arrays are positioned on the right and left sides of the patient's thorax and/or abdomen, respectively (as seen in FIG. 2). An AC voltage generator applies an AC voltage (e.g., 150 kHz) between the front and back transducer arrays for a first interval of time (e.g., one second), which generates an electric field with field lines that generally run in a front/back direction. Then, the AC voltage generator applies an AC voltage at the same frequency between the right and left transducer arrays for a second interval of time (e.g., one second), which generates an electric field with field lines that generally run in a right/left direction. The system then repeats this two-step sequence for the duration of the treatment.

SUMMARY OF THE INVENTION

One aspect of the invention is directed to a first method of applying an alternating electric field to a target region in a person's spinal anatomy. The first method comprises affixing a first set of electrode elements having a first centroid to the person's back with the first centroid positioned adjacent to an upper portion of the person's spine; and affixing a second set of electrode elements having a second centroid to the person's back with the second centroid positioned adjacent to a lower portion of the person's spine. After affixing the first and second sets of electrode elements, an alternating voltage is applied between the first set of electrode elements and the second set of electrode elements.

In some instances of the first method, the electrode elements of the first and second sets are capacitively coupled. In some instances of the first method, the alternating voltage that is applied between the first set of electrode elements and the second set of electrode elements has a frequency between 100 kHz and 300 kHz. In some instances of the first method, the first set of electrode elements comprises a plurality of electrode elements wired in parallel, and the second set of electrode elements comprises a plurality of electrode elements wired in parallel.

In some instances of the first method, the first centroid is positioned at a height between the T8 and T9 vertebra, and the second centroid is positioned at a height between the L3 and L4 vertebra. In some instances of the first method, the first centroid is positioned at a height above the T1 vertebrae, and the second centroid is positioned at a height below the L3 vertebrae.

In some instances of the first method, the alternating electric field has a frequency and field strength that reduces viability of cancer cells in the target region. In some instances of the first method, the alternating electric field has a frequency and field strength that suppresses an autoimmune response in the target region.

Another aspect of the invention is directed to a second method of applying an alternating electric field to a target region in a person's spinal anatomy. The second method comprises affixing a first set of electrode elements having a first centroid to the person's head with the first centroid positioned on an upper surface of the person's head; and affixing a second set of electrode elements having a second centroid to the person's back with the second centroid positioned adjacent to the person's spine. After affixing the first and second sets of electrode elements, an alternating voltage is applied between the first set of electrode elements and the second set of electrode elements.

In some instances of the second method, the electrode elements of the first and second sets are capacitively coupled. In some instances of the second method, the alternating voltage that is applied between the first set of electrode elements and the second set of electrode elements has a frequency between 100 kHz and 300 kHz. In some instances of the second method, the first set of electrode elements comprises a plurality of electrode elements wired in parallel, and the second set of electrode elements comprises a plurality of electrode elements wired in parallel. In some instances of the second method, the first centroid is positioned on the vertex of the head. In some instances of the second method, the second centroid is positioned at a height below the L3 vertebrae.

In some instances of the second method, the alternating electric field has a frequency and field strength that reduces viability of cancer cells in the target region. In some instances of the second method, the alternating electric field has a frequency and field strength that suppresses an autoimmune response in the target region.

Another aspect of the invention is directed to a third method of determining where to position a first set of electrode elements having a first centroid and a second set of electrode elements having a second centroid on a person's body before the first and second sets of electrode elements are used to apply an alternating electric field to a target region in the person's spinal anatomy. The third method comprises identifying a location of a tumor in the person's spinal anatomy; and outputting, based on the identified location, a recommendation for positioning the first and second sets of electrode elements. The recommendation is either (a) to affix the first set of electrode elements to the person's back with the first centroid positioned adjacent to an upper portion of the person's spine, and to affix the second set of electrode elements with the second centroid positioned adjacent to a lower portion of the person's spine or (b) to affix the first set of electrode elements to the person's head with the first centroid positioned on an upper surface of the person's head, and to affix the second set of electrode elements to the person's back with the second centroid positioned adjacent to the person's spine.

In some instances of the third method, the recommendation for positioning the first and second sets of electrode elements is made by (a) simulating affixation of a first set of electrode elements to the person's back at each of a first plurality of positions with the first centroid positioned adjacent to an upper portion of the person's spine, (b) simulating affixation of a second set of electrode elements to the person's back at each of a second plurality of positions with the second centroid positioned adjacent to a lower portion of the person's spine, (c) simulating application of an alternating voltage between the first set of electrode elements and the second set of electrode elements at each of the first plurality of positions and at each of the second plurality of positions, respectively, and (d) determining, based on step (c), which of the first plurality of positions and which of the second plurality of positions results in an optimized alternating electric field in the target region. In some of these instances, step (d) comprises determining which of the first plurality of positions and which of the second plurality of positions (i) maximizes a portion of the target region that has a field strength of at least 1 V/cm, (ii) maximizes uniformity of the field in the target region, or (iii) maximizes the intensity of the field in the target region.

In some instances of the third method, the recommendation for positioning the first and second sets of electrode elements is made by (a) simulating affixation of a first set of electrode elements to the person's head at each of a first plurality of positions with the first centroid positioned on an upper surface of the person's head, (b) simulating affixation of a second set of electrode elements to the person's back at each of a second plurality of positions with the second centroid positioned adjacent to the person's spine, (c) simulating application of an alternating voltage between the first set of electrode elements and the second set of electrode elements at each of the first plurality of positions and at each of the second plurality of positions, respectively, and (d) determining, based on step (c), which of the first plurality of positions and which of the second plurality of positions results in an optimized alternating electric field in the target region. In some of these instances, step (d) comprises determining which of the first plurality of positions and which of the second plurality of positions (i) maximizes a portion of the target region that has a field strength of at least 1 V/cm, (ii) maximizes uniformity of the field in the target region, or (iii) maximizes the intensity of the field in the target region.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
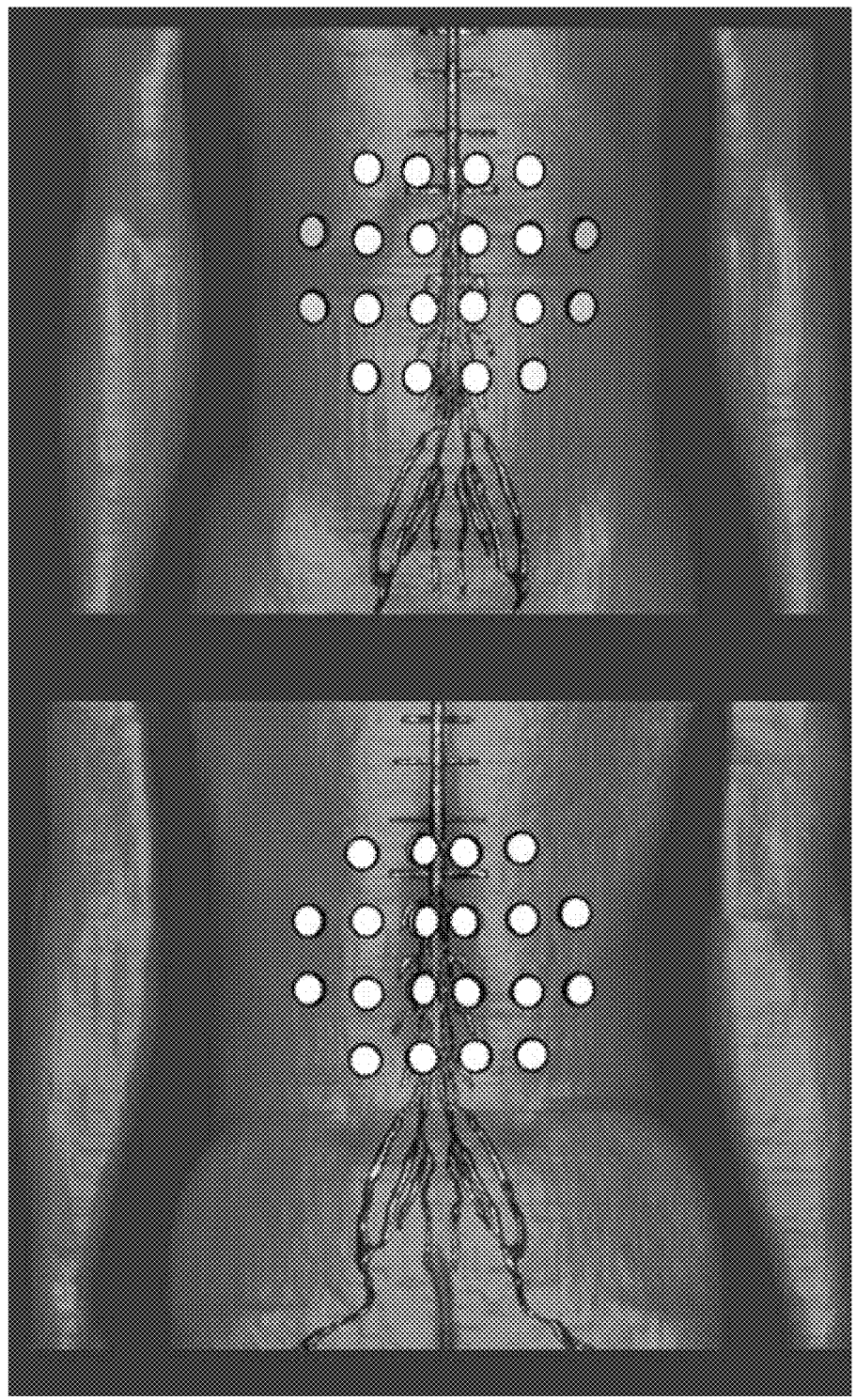
FIG. 1 depicts a prior art approach for positioning a pair of transducer arrays in front/back of a target region in a subject's thorax and/or abdomen to facilitate treatment with TTFields.
Figure 2:
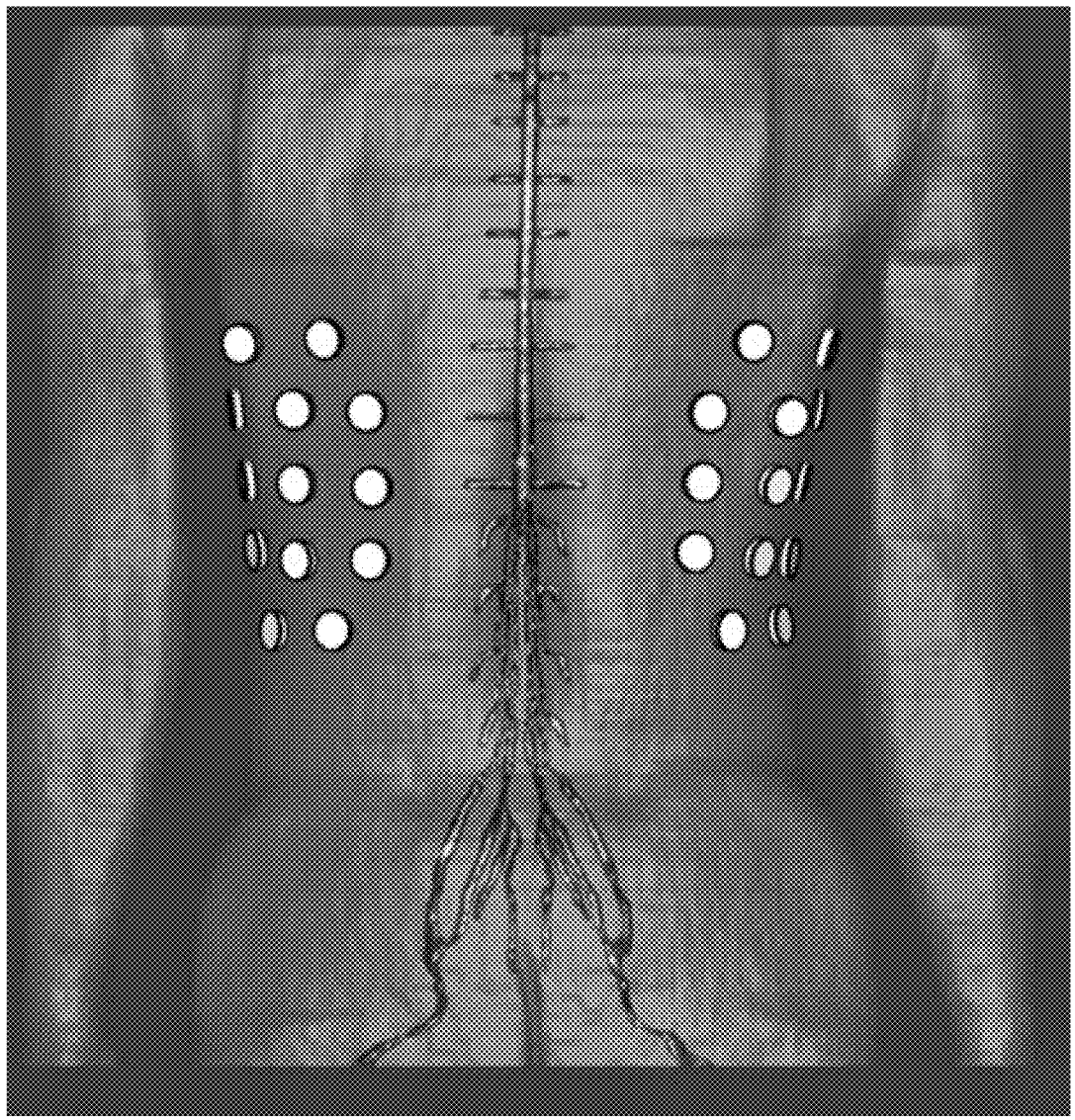
FIG. 2 depicts a prior art approach for positioning a pair of transducer arrays to the right/left of a target region in a subject's abdomen to facilitate treatment with TTFields.

Pre-clinical experiments suggest that in order for TTFields to exert a therapeutic effect, field intensities should exceed a threshold of about 1 V/cm. And in the context of treating abdominopelvic cancers (e.g. pancreatic cancer and ovarian cancer), it is relatively easy to obtain these field intensities by positioning a first pair of transducer arrays in front/back of the target region and a second pair of transducer arrays to the right/left of the target region, as depicted in FIGS. 1 and 2, respectively. The location of the target region (which is the region that is to receive the treatment e.g., to treat cancer or prevent metastases) is typically determined by the treating physician.

As used herein, "spinal anatomy" comprises the spinal cord, vertebrae, spinal discs, spinal nerves, and spinal cerebrospinal fluid.

Many types of cancer (e.g., breast, lung, and prostate) can metastasize to the spinal anatomy. But until now, it was not possible to treat these cancers using TTFields using the prior art layouts for positioning the transducer arrays on a subject's body because the prior art layouts yielded field intensities that were below the therapeutic threshold in significant portions of the spinal anatomy (e.g., the spinal cord).

The inventors have recognized that the spinal anatomy, which has a relatively resistive bone structure that encapsulates a highly conductive layer of fluid (i.e., cerebrospinal fluid), shunts the current delivered across the body by the transducer arrays away from portions of the spinal anatomy (e.g., the spinal cord), reducing the field within it to below the therapeutic threshold. More specifically, numerical simulations show that when the epigastric layouts for the transducer arrays depicted in FIG. 1 was used with a constant current density of 200 mA (pk–pk) per disc at 150 kHz, the average field intensity within the spinal cord was only 0.52 V/cm. And when the lateral layouts for the transducer arrays depicted in FIG. 2 was used with the same current density at 150 kHz, the average field intensity within the spinal cord was only 0.26 V/cm. Both of these field strengths are significantly lower than the recommended 1 V/cm.

Figure 3:
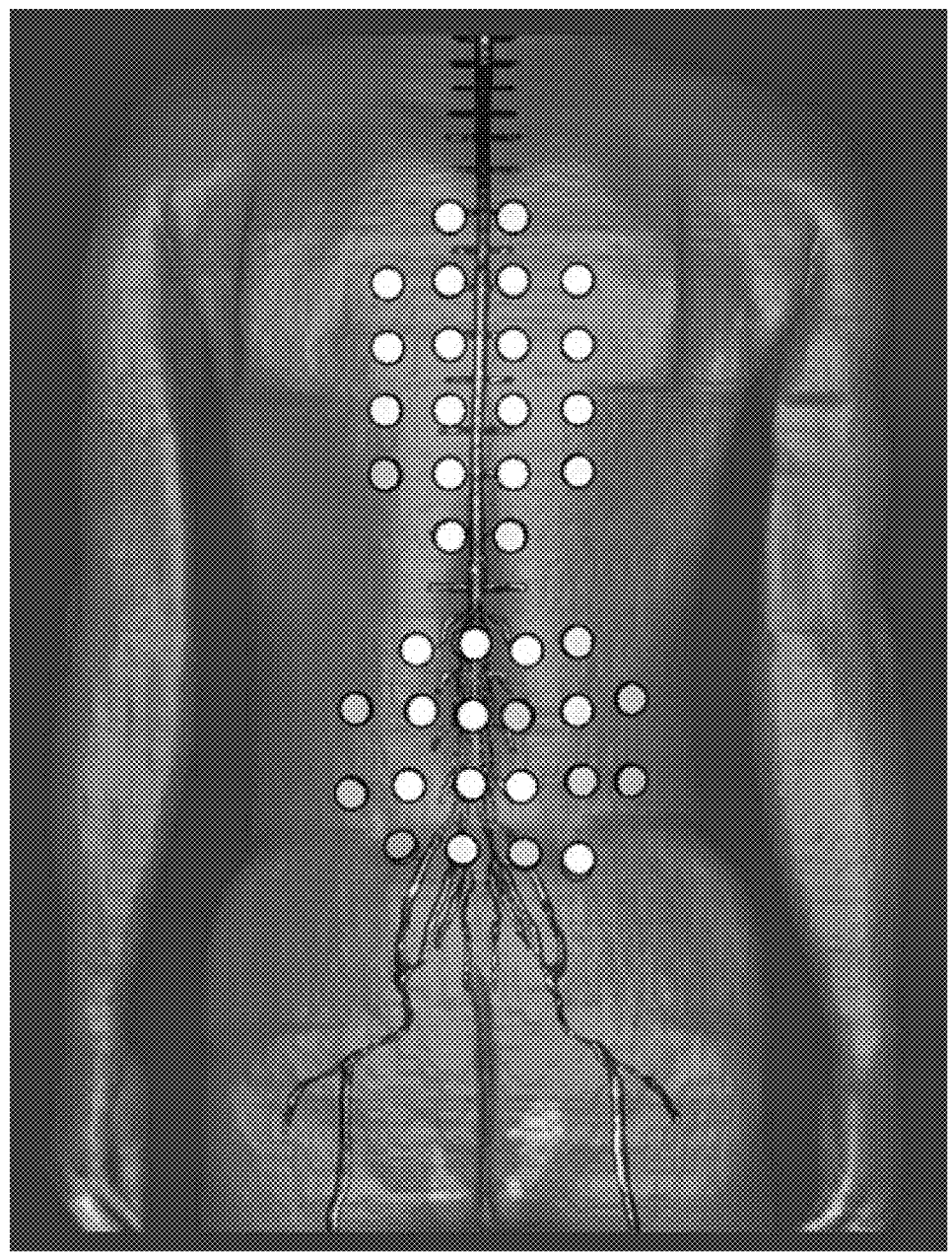
FIG. 3 depicts a first new approach for positioning transducer arrays on a subject's body, with one of the transducer arrays positioned above a target region in the spinal anatomy and the other transducer array positioned below the target region in the spinal anatomy.

FIG. 3 depicts a first new approach for positioning the transducer arrays on a person's body. More specifically, the transducer arrays are positioned on the subject's back as shown in FIG. 3, with one of the transducer arrays positioned above a target region in the spinal anatomy and the other transducer array positioned below the target region in the spinal anatomy. When the transducer arrays are positioned in this manner and an AC voltage is applied between the upper and lower transducer arrays, provide field intensities above 1 V/cm can be achieved in the spinal cord.

In the exemplary embodiment depicted in FIG. 3, the upper transducer array is positioned on the subject's back with its centroid located between the T8 and T9 vertebra, and the lower transducer array is positioned on the subject's back with its centroid located between the L3 and L4 vertebra. The target region in the spinal anatomy lies between those two centroids. With this configuration, part of the electric current flows through the spinal anatomy, inducing a higher electric field within the spinal cord and surrounding CSF. More specifically, numerical simulations for this transducer array layout reveal that when an AC voltage is applied between the upper and lower transducer arrays with a constant current density of 200 mA (pk–pk) per disc at 150 kHz, the average field intensity within the target region in the spinal cord was 1.89 V/cm. This exceeds the values obtainable using the epigastric and lateral layouts by factors of 3.5× and 7×, respectively. In addition, using the FIG. 3 layout for the transducer array resulted in an average field intensity in the nerves that extend from the spinal cord of 1.64 V/cm.

A variation of the approach depicted in FIG. 3 may be used to treat the entire spinal cord and surrounding CSF by positioning the upper transducer array at the neck (e.g. above the T1 vertebrae) and positioning the lower transducer array near the bottom of the spine (e.g., below the L3 vertebrae).

Figure 4:
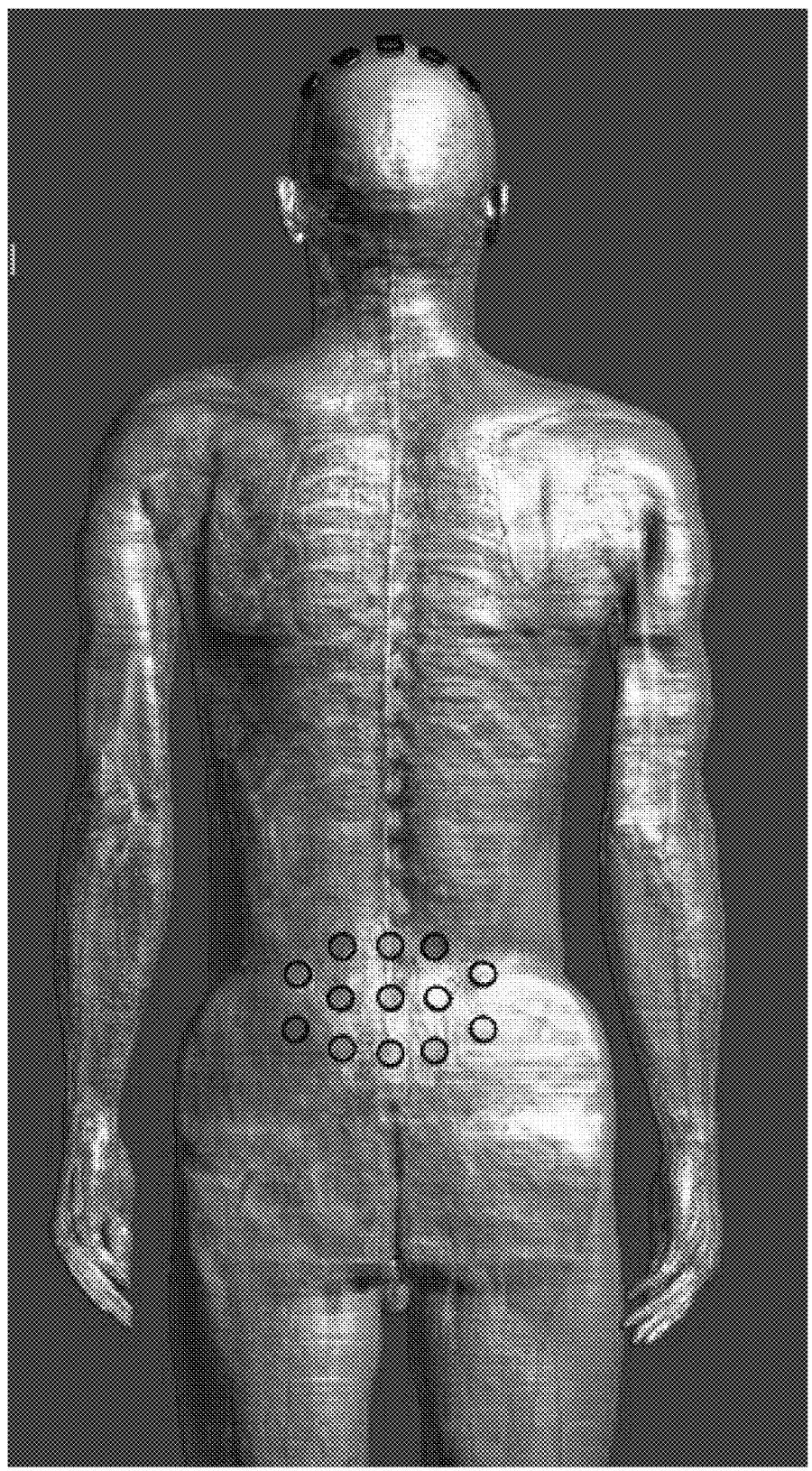
FIG. 4 depicts a rear view of a second new approach for positioning transducer arrays on a subject's body, with one of the transducer arrays positioned on an upper surface of the person's head and another one of the transducer arrays positioned adjacent to the person's spine.

FIG. 4 depicts a second new approach for positioning the transducer arrays on a person's body. More specifically, the transducer arrays are positioned on the subject's body as shown in FIG. 4, with one of the transducer arrays positioned centered on top of the subject's head and the other transducer array positioned on the subject's back with its centroid located below the L3 vertebra.

Figure 5A:
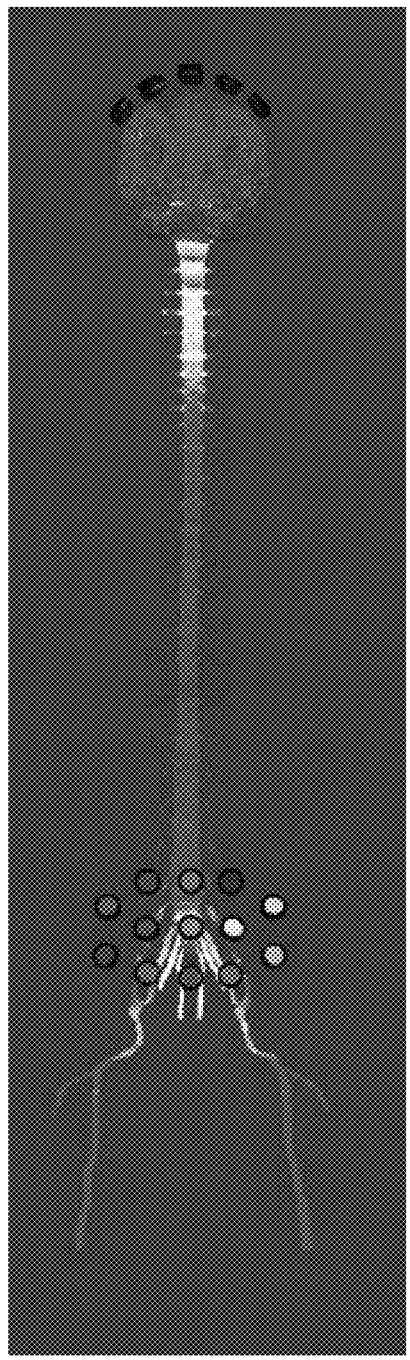
FIGS. 5A and 5B depict rear and side views, respectively, of numerical simulations for the transducer array layout shown in FIG. 4.
Figure 5B:
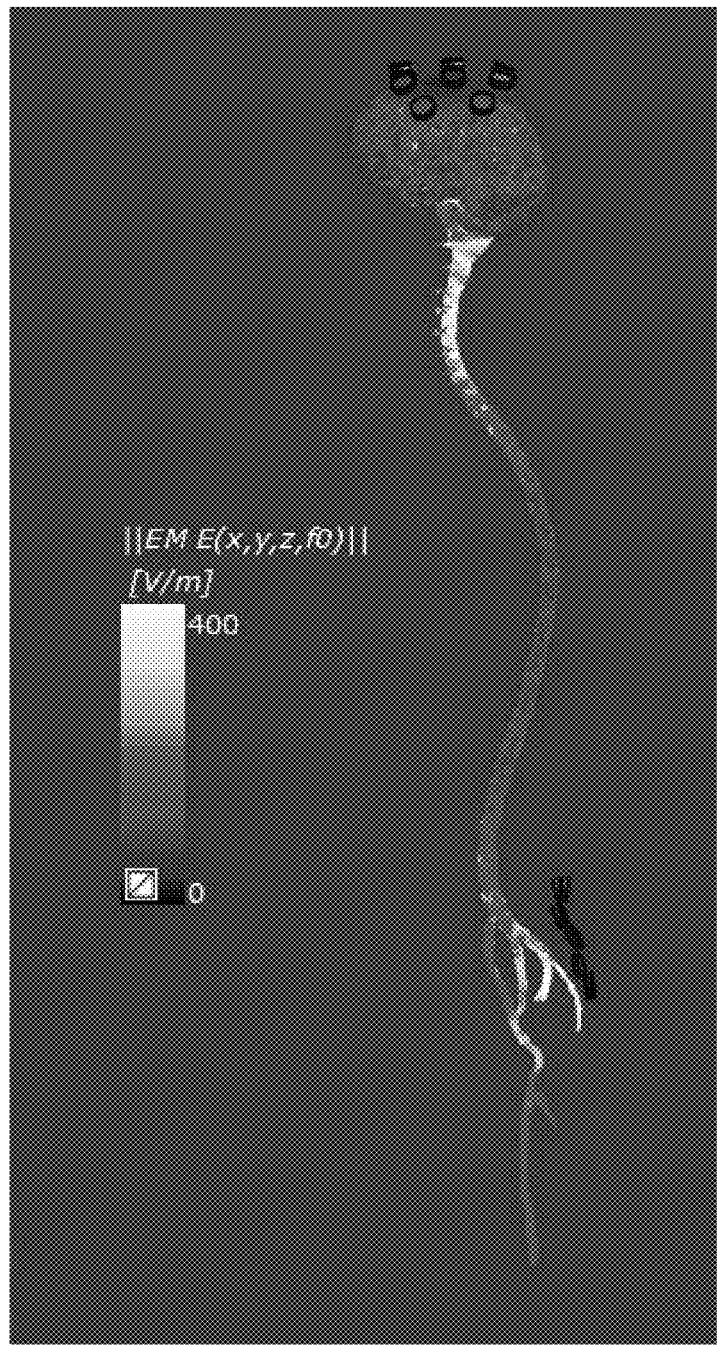

With this configuration, part of the electric current flows through the brain and spinal anatomy, inducing a higher electric field within the spinal cord and surrounding CSF. The results of numerical simulations for this transducer array layout are depicted in FIGS. 5A and 5B for rear and side views, respectively. These results reveal that when an AC voltage is applied between the upper and lower transducer arrays with a constant current density of 200 mA (pk–pk) per disc, the mean field intensity in the spinal cord, nerves, and CSF was 1.37 V/cm, and the mean field intensity in the CSF (taken alone) was 1.24 V/cm. Here again, these values dramatically exceed the values obtainable using the epigastric and lateral layouts described above in connection with FIGS. 1 and 2, and also exceed the recommended 1 V/cm threshold.

The same construction for the transducer arrays that is used in other anatomic locations may be used when the transducer arrays are positioned near the upper and lower portions of the spine in the FIG. 3 embodiment. Examples of conventional transducer arrays are the transducer arrays used with the Novocure Optune® system. These transducer arrays have a flexible backing that is configured for affixation to person's body. Suitable materials for the flexible backing include cloth, foam, and flexible plastic (e.g., similar to corresponding materials used in bandages). A plurality of capacitively coupled electrode elements are positioned on the inner side of the flexible backing, and each of the capacitively coupled electrode elements has a conductive plate with a dielectric layer disposed thereon that faces inward. Optionally, temperature sensors (e.g., thermistors) may be positioned beneath each of the electrode elements in a manner that is similar to the conventional arrangement used in the Novocure Optune® system.

A set of conductors connects to the conductive plates of each of the plurality of capacitively coupled electrode elements. The conductors may be implemented using, for example, discrete wiring or using traces on a flex circuit. A layer of adhesive is configured to hold portions of the flexible backing that are not covered by any of the electrode elements against the person's body.

Note that in the embodiments depicted in FIG. 3, each transducer array includes 20 individual electrode element discs arranged in four rows with 4 elements per row, and an additional two rows with 2 elements per row. But in alternative embodiments, different layouts and/or a different number of individual electrode elements (e.g., between 4 and 24) may be used. Examples include, but are not limited to, transducer arrays that each have 9 electrode elements using any suitable layout (e.g., arranged in three rows with 3 elements per row) and transducer arrays that each have 13 electrode elements using any suitable layout (e.g., arranged in three rows with 3 elements per row, plus an additional two rows with 2 elements per row).

Similarly, in the embodiments depicted in FIG. 4, each transducer array includes 13 individual electrode element discs arranged in three rows with 3 elements per row, and an additional two rows with 2 elements per row. But in alternative embodiments, a different number of individual electrode elements (e.g., between 4 and 24) may be used.

After affixing the first and second sets of electrode elements as described above, an alternating voltage is applied between the first set of electrode elements and the second set of electrode elements. In some embodiments, the frequency of the alternating voltage is between 100 kHz and 300 kHz. In some embodiments, the frequency of the alternating voltage is 150 kHz.

Advantageously, the layouts described herein can be used to deliver alternating electric fields at therapeutically effective levels (i.e., greater than 1 V/cm) in portions of the spinal anatomy where those therapeutically effective levels were previously unobtainable. This can be beneficial in a variety of contexts including treating existing tumors in portions of the spinal anatomy that were previously untreatable, preventing metastases that may arise in portions of the spinal anatomy, and suppressing an autoimmune response in portions of the spinal anatomy.

The positions of each set of electrode elements may be varied from the exact locations depicted in the figures, as long as the movement is small enough so that the respective anatomic description above remains unchanged. For example, in the FIG. 3 embodiment, the upper set of electrode elements can move up, down, or to either side, as long as its centroid is positioned on the person's back adjacent to an upper portion of the person's spine. Similarly, the lower set of electrode elements can move up, down, or to either side, as long as its centroid is positioned on the person's back adjacent to a lower portion of the person's spine. In the FIG. 4/5 embodiment, the upper set of electrode elements can move around on the person's head as long as the first centroid is positioned on an upper surface of the person's head; and the lower set of electrode elements can move around on the person's back as long as the second centroid is positioned adjacent to the person's spine.

Within this limited range of movement, the optimum position of each of the sets of electrode elements may be determined using simulations (e.g., finite element simulations) for each individual person to calculate the resulting electric field for each combination of positions for the various sets of electrodes, and selecting the combination that provides the best results (e.g., a layout in which the largest portion of a target region has a field strength of at least 1 V/cm, a layout with the highest uniformity of the field in a target region, or a layout that maximizes the intensity of the field in a target region). An indication of the selected combination is then output to the care provider using, for example, a suitable display or printout. The care provider will then apply the sets of electrode elements to the person at the positions indicated by the output, hook the sets of electrode elements up to an AC signal generator, and commence treatment.

A recommended position of each of the sets of electrode elements may also be generated without simulations by identifying a location of a tumor in the person's spinal anatomy; and outputting, based on the identified location (e.g., using a lookup table), a recommendation for positioning the first and second sets of electrode elements. The recommendation is either (a) to affix the first set of electrode elements to the person's back with the first centroid positioned adjacent to an upper portion of the person's spine, and to affix the second set of electrode elements with the second centroid positioned adjacent to a lower portion of the person's spine (as depicted in FIG. 3) or (b) to affix the first set of electrode elements to the person's head with the first centroid positioned on an upper surface of the person's head, and to affix the second set of electrode elements to the person's back with the second centroid positioned adjacent to the person's spine (as depicted in FIG. 4). An indication of the selected combination is then output to the care provider using, for example, a suitable display or printout. The care provider will then apply the sets of electrode elements to the person at the positions indicated by the output, hook the sets of electrode elements up to an AC signal generator, and commence treatment.

An additional aspect of the invention is directed to a first computer-readable media upon which computer-executable instructions are stored. When the instructions are executed by a processor, the processor will determine where to position a first set of electrode elements having a first centroid and a second set of electrode elements having a second centroid on a person's body before the first and second sets of electrode elements are used to apply an alternating electric field to a target region in the person's spinal anatomy. The processor will accomplish this by identifying a location of a tumor in the person's spinal anatomy; and outputting, based on the identified location, a recommendation for positioning the first and second sets of electrode elements, wherein the recommendation is either (a) to affix the first set of electrode elements to the person's back with the first centroid positioned adjacent to an upper portion of the person's spine, and to affix the second set of electrode elements with the second centroid positioned adjacent to a lower portion of the person's spine or (b) to affix the first set of electrode elements to the person's head with the first centroid positioned on an upper surface of the person's head, and to affix the second set of electrode elements to the person's back with the second centroid positioned adjacent to the person's spine.

Optionally, when the computer-executable instructions stored on the first computer-readable media are executed by the processor, the recommendation that is made by the processor for positioning the first and second sets of electrode elements is made by (a) simulating affixation of a first set of electrode elements to the person's back at each of a first plurality of positions with the first centroid positioned adjacent to an upper portion of the person's spine, (b) simulating affixation of a second set of electrode elements to the person's back at each of a second plurality of positions with the second centroid positioned adjacent to a lower portion of the person's spine, (c) simulating application of an alternating voltage between the first set of electrode elements and the second set of electrode elements at each of the first plurality of positions and at each of the second plurality of positions, respectively, and (d) determining, based on step (c), which of the first plurality of positions and which of the second plurality of positions results in an optimized alternating electric field in the target region. Optionally, in these embodiments, step (d) may comprise determining which of the first plurality of positions and which of the second plurality of positions (i) maximizes a portion of the target region that has a field strength of at least 1 V/cm, (ii) maximizes uniformity of the field in the target region, or (iii) maximizes the intensity of the field in the target region.

Optionally, when the computer-executable instructions stored on the first computer-readable media are executed by the processor, the recommendation that is made by the processor for positioning the first and second sets of electrode elements is made by (a) simulating affixation of a first set of electrode elements to the person's head at each of a first plurality of positions with the first centroid positioned on an upper surface of the person's head, (b) simulating affixation of a second set of electrode elements to the person's back at each of a second plurality of positions with the second centroid positioned adjacent to the person's spine, (c) simulating application of an alternating voltage between the first set of electrode elements and the second set of electrode elements at each of the first plurality of positions and at each of the second plurality of positions, respectively, and (d) determining, based on step (c), which of the first plurality of positions and which of the second plurality of positions results in an optimized alternating electric field in the target region. Optionally, in these embodiments, step (d) may comprise determining which of the first plurality of positions and which of the second plurality of positions (i) maximizes a portion of the target region that has a field strength of at least 1 V/cm, (ii) maximizes uniformity of the field in the target region, or (iii) maximizes the intensity of the field in the target region.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of applying an alternating electric field to a target region in a person's spinal anatomy, the method comprising:

affixing a first set of electrode elements having a first centroid to the person's back with the first centroid positioned adjacent to an upper portion of the person's spine;

affixing a second set of electrode elements having a second centroid to the person's back with the second centroid positioned adjacent to a lower portion of the person's spine; and applying an alternating voltage between the first set of electrode elements and the second set of electrode elements to impose a tumor treating field in the target region in the person's spinal anatomy, wherein the applying is performed after affixing the first and second sets of electrode elements.

2. The method of claim 1, wherein the electrode elements of the first and second sets are capacitively coupled.

3. The method of claim 1, wherein the alternating voltage that is applied between the first set of electrode elements and the second set of electrode elements has a frequency between 100 kHz and 300 kHz.

4. The method of claim 1, wherein the first set of electrode elements comprises a plurality of electrode elements wired in parallel, and wherein the second set of electrode elements comprises a plurality of electrode elements wired in parallel.

5. The method of claim 1, wherein the first centroid is positioned at a height between the T8 and T9 vertebra, and wherein the second centroid is positioned at a height between the L3 and L4 vertebra.

6. The method of claim 1, wherein the first centroid is positioned at a height above the T1 vertebrae, and wherein the second centroid is positioned at a height below the L3 vertebrae.

7. The method of claim 1, wherein the alternating electric field has a frequency and field strength that reduces viability of cancer cells in the target region.

8. The method of claim 1, wherein the alternating electric field has a frequency and field strength that suppresses an autoimmune response in the target region.

\* \* \* \* \*